(12) United States Patent
Bertocci et al.

(10) Patent No.: US 11,938,514 B2
(45) Date of Patent: Mar. 26, 2024

(54) CURVED SHAPE PIEZOELECTRIC TRANSDUCER AND METHOD FOR MANUFACTURING THE SAME

(71) Applicant: Esaote S.p.A., Genoa (IT)

(72) Inventors: Francesco Bertocci, Santa Maria a Monte (IT); Ramona De Luca, Florence (IT)

(73) Assignee: Esaote S.p.A., Genoa (IT)

(*) Notice: Subject to any disclaimer, the term of this patent is extended or adjusted under 35 U.S.C. 154(b) by 53 days.

(21) Appl. No.: 17/226,946

(22) Filed: Apr. 9, 2021

(65) Prior Publication Data

US 2022/0152653 A1   May 19, 2022

(30) Foreign Application Priority Data

Apr. 14, 2020 (EP) .................................. 20169260

(51) Int. Cl.
| | | |
|---|---|---|
| *B06B 1/06* | (2006.01) | |
| *A61B 8/00* | (2006.01) | |
| *G10K 11/32* | (2006.01) | |
| *H04R 17/00* | (2006.01) | |

(52) U.S. Cl.
CPC ............ *B06B 1/0622* (2013.01); *G10K 11/32* (2013.01); *H04R 17/005* (2013.01); *A61B 8/4494* (2013.01)

(58) Field of Classification Search
CPC .......................... A61B 8/4494; G01S 7/52079
See application file for complete search history.

(56) References Cited

U.S. PATENT DOCUMENTS

| | | |
|---|---|---|
| 4,825,115 A | 4/1989 | Kawabe et al. |
| 5,267,221 A | 11/1993 | Miller et al. |
| 5,329,498 A | 7/1994 | Greenstein |

(Continued)

OTHER PUBLICATIONS

Extended European Search Report dated Oct. 1, 2020, which issued in corresponding EP Patent Application No. 20169260.5-1001.

(Continued)

*Primary Examiner* — Colin T. Sakamoto
*Assistant Examiner* — Tommy T Ly
(74) *Attorney, Agent, or Firm* — Dickinson Wright PLLC

(57) ABSTRACT

Transducer assembly transmits ultrasonic energy towards a zone acoustically coupled to an object or area of interest, and comprises a piezoelectric subassembly matching a curved support layer disposed behind said subassembly. Piezoelectric subassembly comprises piezoelectric elements and metal connections. Piezoelectric elements are disposed along a first azimuth direction to form parallel curved segments of piezoelectric elements extending in a second elevation direction, each being in contact with a corresponding metal connection extending in the elevation direction for transmitting/receiving electric signals to/from each piezoelectric segment. The subassembly has a a central part comprising piezoelectric material and a lateral part comprising resin material incorporating the metal connections so that each curved segment results in a sequence of resin/piezoelectric/resin materials disposed along the elevation direction with the extension and curvature of the piezoelectric material in the central part defining the elevation focussing of the transducer assembly. A corresponding manufacturing process is also disclosed.

10 Claims, 10 Drawing Sheets

(56) References Cited

U.S. PATENT DOCUMENTS

| | | | |
|---|---|---|---|
| 5,792,058 A | | 8/1998 | Lee et al. |
| 6,822,374 B1* | | 11/2004 | Smith .................... B06B 1/064 |
| | | | 310/334 |
| 7,792,058 B1 | | 9/2010 | Yip et al. |
| 9,345,450 B2 | | 5/2016 | Corl |
| 2010/0168583 A1* | | 7/2010 | Dausch ................ B06B 1/0622 |
| | | | 600/466 |
| 2015/0297191 A1 | | 10/2015 | Beers |
| 2015/0305714 A1* | | 10/2015 | Spigelmyer ......... G01S 7/52079 |
| | | | 600/443 |
| 2017/0360415 A1* | | 12/2017 | Rothberg ................. A61B 8/54 |
| 2018/0290175 A1* | | 10/2018 | Palchetti ............... B06B 1/0677 |
| 2021/0186461 A1* | | 6/2021 | Katsura ................ B06B 1/0622 |

OTHER PUBLICATIONS

Anonymous: "Ultrasound Physics including wave propagation, transducer, imaging instrumentation, Color Doppler Flow Image, regulations on acoustic output", Apr. 18, 2015, XP055730534, Retrieved from the Internet: URL:https://web.archive.org/web/20150418050307/http://www.biosono.com/UltrPhys/UltrPhysMain.htm [retrieved on Sep. 14, 2020].

* cited by examiner

CURVED SHAPE PIEZOELECTRIC TRANSDUCER AND METHOD FOR MANUFACTURING THE SAME

FIELD

The disclosure relates to the technical field of ultrasound probes, particularly in the medical field, although it can find applications also in the non-destructive testing field.

RELATED ART

Ultrasound diagnostic technology generally relates to imaging of biological tissue using an ultrasonic transducer probe. The probe includes a transducer which transmits ultrasonic waves and receives ultrasonic echoes reflected from the tissue. The transducer is typically placed on the body surface or internal to a body lumen of a patient in a selected imaging region. The ultrasound transducer generates and directs ultrasonic waves to the imaging region. The transducer then receives ultrasonic waves reflected from the region and converts the received waves into electrical signals that are processed to form a diagnostic image.

Ultrasound transducers typically have several acoustical stacks or layers arranged in one dimension (1D) or in two-dimensional (2D) arrays from the furthest (back) to the closest (front) to the area to be placed in contact with the skin and in more in general with the surface of the object to be analysed.

One or more of these layers comprise piezoelectric elements capable of converting a signal into acoustic waves and vice versa. The remaining layers consist of a backing layer placed between the piezoelectric element and the back of the probe and one or more matching layers located between the piezoelectric elements and the front of the probe.

In order to image a sector slice of the body, a steerable ultrasound beam is generated by driving the elements of the array with waveforms having different delays according to well-known focusing law. In case of 2D arrays, beam steering is achieved in two planes crossing orthogonally the array, so called azimuthal plane and elevation plane. In case of 1D arrays, electronic beam steering is affected on the azimuth plane, i.e. the plane passing through the main axis of the array, while focusing on the elevation plane, i.e. on the plane orthogonal to the azimuth plane, is achieved by using an acoustic lens or by curving the array on the elevation direction as taught by U.S. Pat. No. 5,792,058. Intermediate solutions exist like in 1.25D, 1.5D, 1.75D arrays where a partial electronic elevation focusing is achieved by electronically steering along the elevation direction which is populated by a number of rows of transducer elements.

The present disclosure is directed to transducer arrays of any type achieving, or improving, elevation focusing by using curved structures.

As exemplary shown in FIG. 4, in order to achieve a curved shaped, the piezoelectric material 120 has to be pressed on a backing support member 100 having a complementary curved shaped, before stacking the matching layer (s) 130, making connections 110 and applying acoustic lens 140.

Press fitting is achieved through a member (not shown in the figure) that pushes a planar flexible layer of composite piezoelectric material 120 against the curved backing support member 100 with interposition of a bonding material 150 as shown in FIG. 5. If the planar layer of composite is wide enough, the piezoelectric material tends to follow the curvature of the backing. If the dimensions are reduced, increased tensile forces determine a non-perfect and non-parallel bending. The result is a non-uniform gap between the curved piezoelectric layer and the backing which leads to a non-uniform distribution of the bonding material.

Non-homogeneous distribution of bonding material may lead to artefacts in the final images and poor sensitivity. This is even more evident in high frequency applications where structures, particularly the piezoelectric layer, are of reduced dimensions (when the frequency increases, the wavelength decreases and thus also the overall dimension of the transducer decreases).

Furthermore, a small piezoelectric layer in terms of elevation and thickness, as in high frequency applications, offers a small surface to the pushing member and thus receives a less uniform pressure resulting in a transducer more sensitive to inhomogeneities of bonding layers and thus prone to acoustic artefacts.

SUMMARY

It is thus an object of embodiments herein to provide curved acoustic stacks with bonding lines between layers having improved homogeneity and thickness.

In an embodiment, a transducer assembly operable to transmit ultrasonic energy in a desired direction towards a zone adapted to be acoustically coupled to an object or area of interest comprises a piezoelectric subassembly matching a curved support layer, for example a backing layer or an acoustic mirror stacked over a backing layer, disposed behind said piezoelectric subassembly with respect to the desired direction, wherein the piezoelectric subassembly comprise piezoelectric elements and metal connections, wherein the piezoelectric elements are disposed along a first direction, so-called azimuth direction, to form a number of parallel curved segments of piezoelectric elements extending in a second direction, so-called elevation direction, each piezoelectric segment being in contact with a corresponding metal connection extending in the elevation direction for transmitting/receiving electrical signals to/from each piezoelectric segment. The subassembly comprises a central part and a lateral part extending from the central part, wherein the central part comprises piezoelectric material and the lateral part comprises a resin material incorporating the metal connections so that each curved segment results substantially in a sequence of resin/piezoelectric/resin materials disposed along the elevation direction with the extension and curvature of the piezoelectric material disposed in the central part of the subassembly defining the elevation focusing of the transducer assembly.

The central part of the subassembly typically comprises more than 90%, preferably more than 95%, more preferably more than 97%, of the whole piezoelectric material forming the subassembly and typically occupies an area having an extension which varies from 40% to 70%, particularly from 50% to 60%, of the whole extension of the subassembly. The relation between area covered by the central part and area covered by the lateral part is function of the aperture of the transducer assembly in the elevation direction.

This structure allows not only to reduce inhomogeneities in the bonding line, but also to vary the mechanical focus in the elevation plane without changing the backing support. By acting on the dimension of the central part of the subassembly, still maintaining the same overall encumbrance to match the backing block, it is, in fact, possible to vary the aperture of the transducer array and thus the focus. This is highly advantageous as it allows to provide kits comprising a curved backing layer having a predetermined curvature and a plurality of piezoelectric subassemblies having the same dimensions but different central part/lateral part area ratio to implement different elevation focussing within transducer assemblies of the same dimensions, i.e. tuning the elevation focus without changing the dimension and the structure of the probe assembly.

This is advantageous also in conventional ultrasound probes comprising an acoustic lens and a matching layer stacked over a transducer assembly. In this case, the ratio between the central and the lateral part of the transducer assembly is advantageously considered in function of the acoustic/geometric characteristics of the acoustic lens to take into account that elevation focusing is achieved partly by such lens and partly by the curved structure.

The dimension of the elevation dimension of each curved piezoelectric element of the transducer assembly can be fine-tuned by grinding/etching opposite lateral parts of a piezoelectric block or providing a pre-formed matrix of composite material and resin material with the composite material substantially located in the middle of the subassembly to form the active part of the transducer assembly for transmitting/receiving electrical signals. The matrix has a side facing the support layer where a bonding material is interspersed.

An embodiment also relates to a composite-based piezoelectric subassembly for manufacturing a transducer assembly according to embodiments herein. The subassembly comprises a planar composite-based element having a piezoelectric central part with metal connections and lateral parts extending from the central part and comprising a resin material incorporating the metal connections to form a number of transducer elements along a first direction, so-called azimuth direction, having a sequence of resin/piezoelectric/resin materials along a second direction, so-called elevation direction, function of the aperture of the transducer assembly to be manufactured.

Embodiments also relate to process for manufacturing a transducer assembly operable to transmit ultrasonic energy in a desired direction towards a zone adapted to be acoustically coupled to an object or area of interest, the process comprising:
  providing a planar piezoelectric layer having metal connections forming a number of transducer elements along a first direction, so-called azimuth direction;
  providing a curved support layer;
  providing a flexible printed circuit (FPC);
  soldering the flexible printed circuit on the metal connections;
  pushing the piezoelectric layer on the support layer with interposition of a bonding material to obtain a curved piezoelectric layer bonded on the support;
  grinding/etching a lateral part of the piezoelectric layer to form a subassembly comprising a central part and lateral parts extending from the central part;
  filling the grinded/etched lateral part with a resin material so that each transducer element results substantially in a sequence of resin/piezoelectric/resin materials disposed along a second direction, so-called elevation direction, with the extension and curvature of the piezoelectric material disposed in the central part of the subassembly defining the elevation focussing of the transducer assembly.

At the end of the grinding/etching step, the central part preferably comprises more than 90%, preferably more than 95%, more preferably more than 97%, of the piezoelectric material forming the whole subassembly.

The grinding/etching step advantageously comprises grinding/etching an area of the piezoelectric layer having a controlled extension to obtain a transducer assembly operable with a predetermined elevation focus.

Further embodiments relate to a process for manufacturing a transducer assembly operable to transmit ultrasonic energy in a desired direction towards a zone adapted to be acoustically coupled to an object or area of interest, the process comprising:
  providing a planar piezoelectric subassembly having a piezoelectric central part with metal connections and a lateral part extending from the central part and comprising a resin material incorporating the metal connections to form a number of transducer elements along a first direction, so-called azimuth direction, having a sequence of resin/piezoelectric/resin materials along a second direction, so-called elevation direction;
  providing a curved support layer;
  providing a flexible printed circuit (FPC);
  soldering the flexible printed circuit on the metal connections;
  pushing the piezoelectric subassembly on the support layer with interposition of a bonding material to obtain a curved piezoelectric subassembly wherein the extension and curvature of the piezoelectric material disposed in the central part of the subassembly defines the elevation focussing of the transducer assembly.

The relation between the area covered by the central part and the area covered by the lateral part of the subassembly is tuned as a function of the aperture of the transducer assembly in the elevation direction to be realized.

The process may further comprise bonding or casting a matching layer and an acoustic lens to the subassembly to obtain an acoustic stack having the following order from the furthest to the closest to the zone adapted to be acoustically coupled to the object: backing layer, piezoelectric layer, matching layer, lens layer. In this case, the area covered by the central part and the area covered by the lateral part of the subassembly are dimensioned by considering the acoustic/geometric properties of the acoustic lens.

Further improvements will form the subject of the dependent claims.

BRIEF DESCRIPTION OF THE DRAWINGS

The characteristics of example embodiments and the advantages derived therefrom will be more apparent from the following description of non-limiting embodiments, illustrated in the annexed drawings, in which.

DETAILED DESCRIPTION OF PREFERRED EMBODIMENTS

Figure 1:
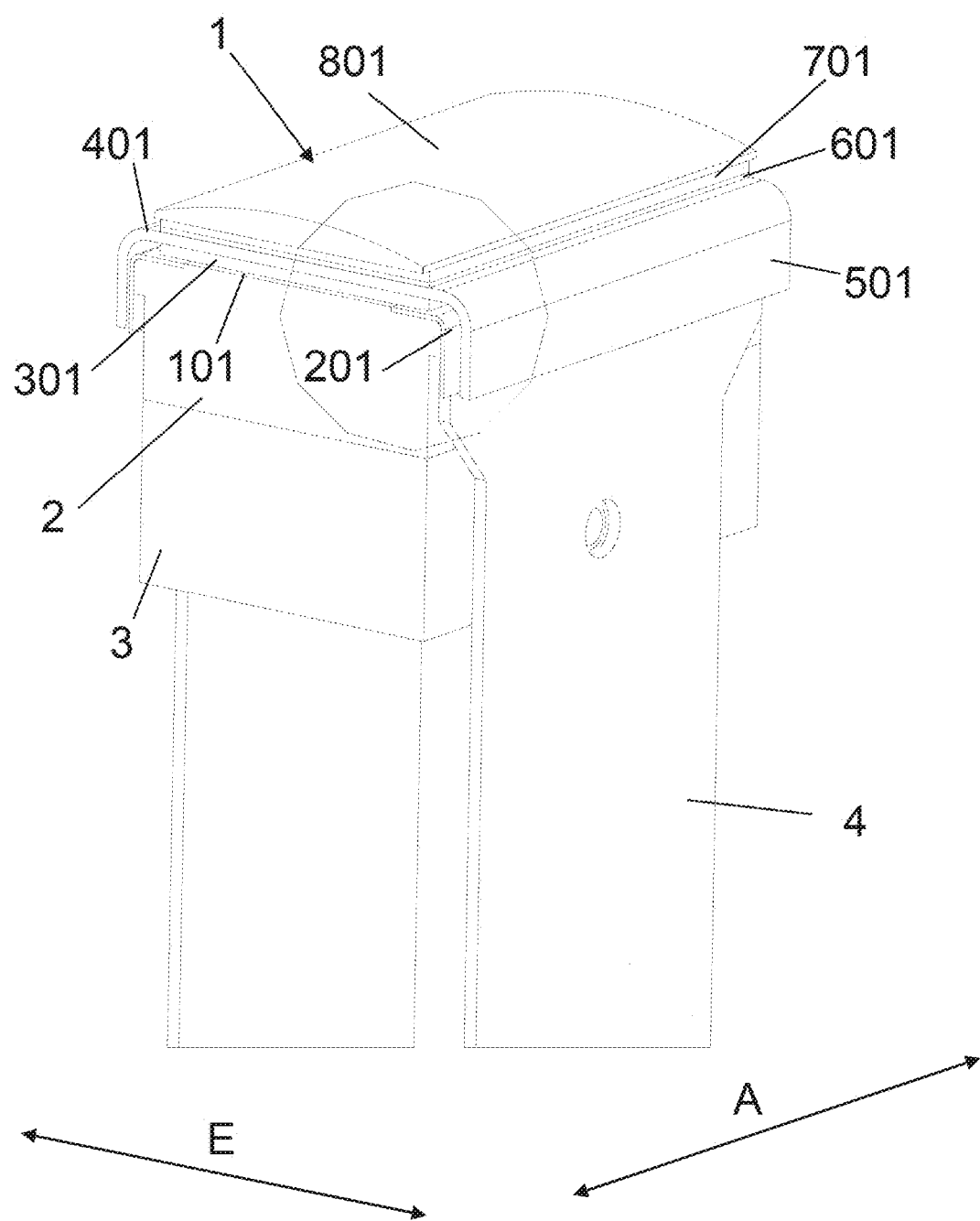
FIG. 1 shows a perspective view of a conventional probe according to the state of the art.
Figure 2:
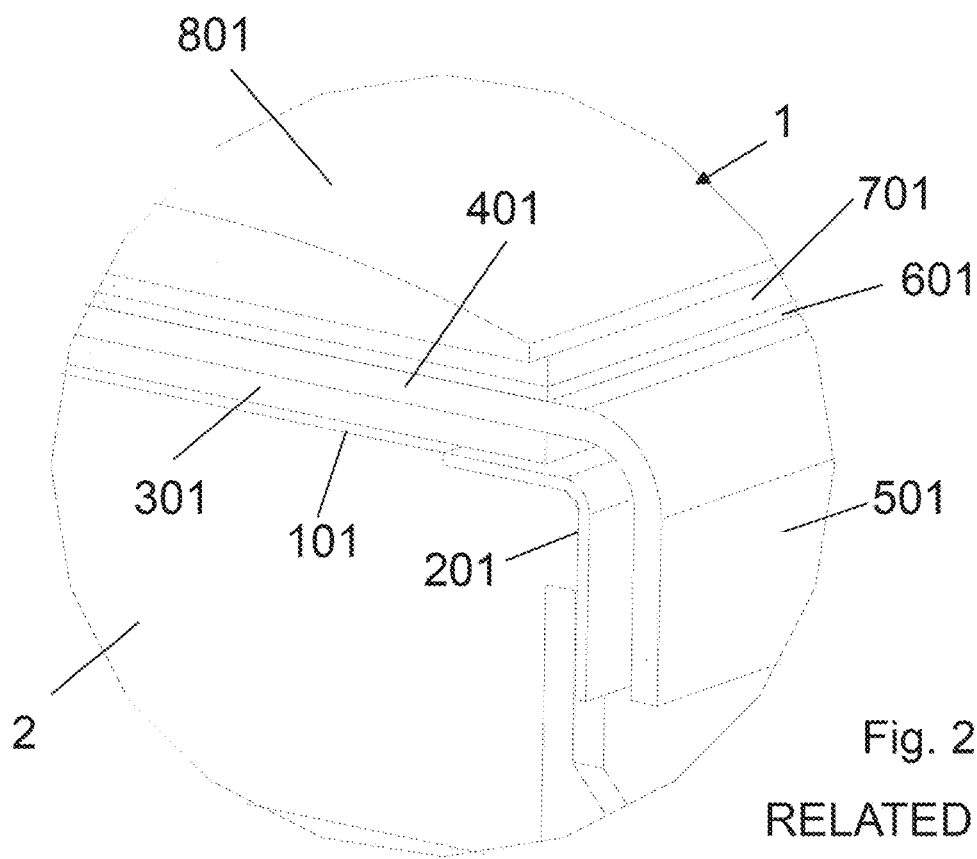
FIG. 2 shows an enlarged view of the head of the probe according to FIG. 1.
Figure 3:
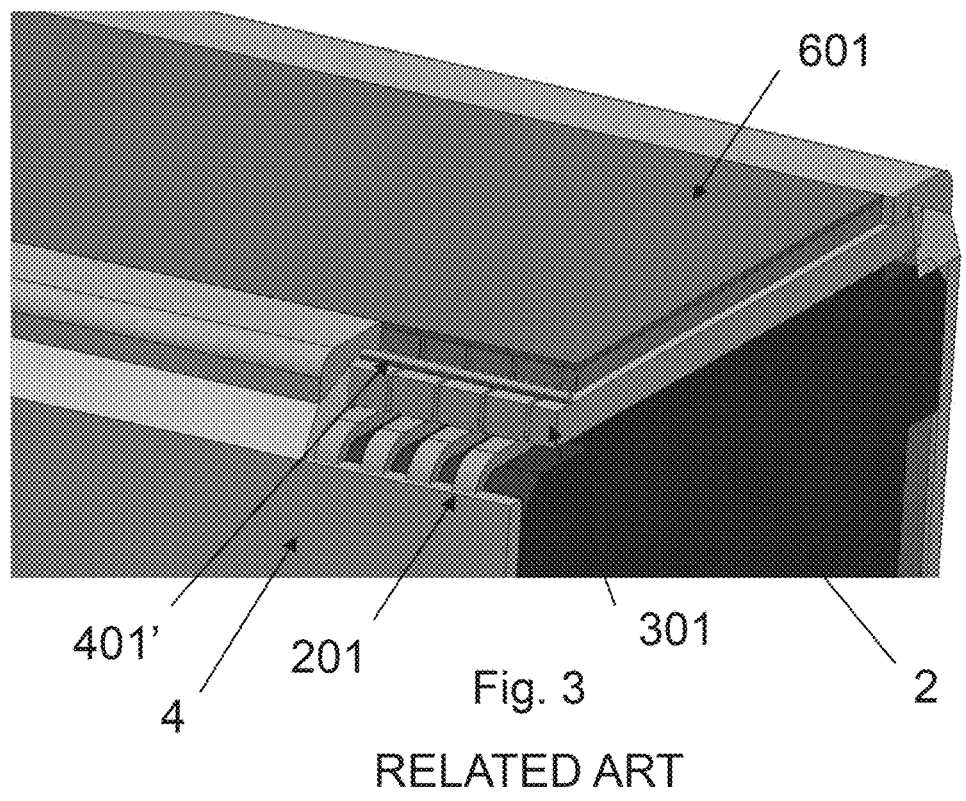
FIG. 3 schematically shows a probe head with ground wire connections arranged to contact transducer elements of a same row.
Figure 4:
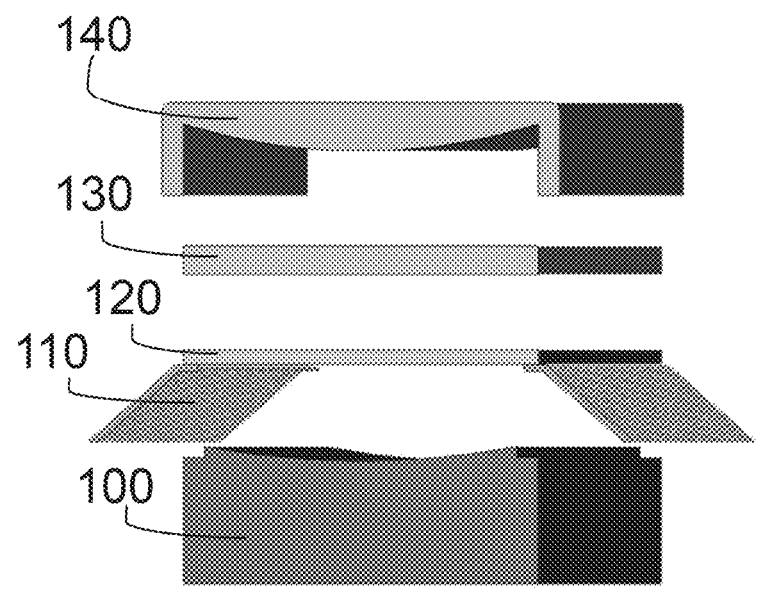
FIG. 4 schematically shows the cross section of a conventional ultrasound transducer before press fitting a planar piezoelectric material on a curved backing.
Figure 5:
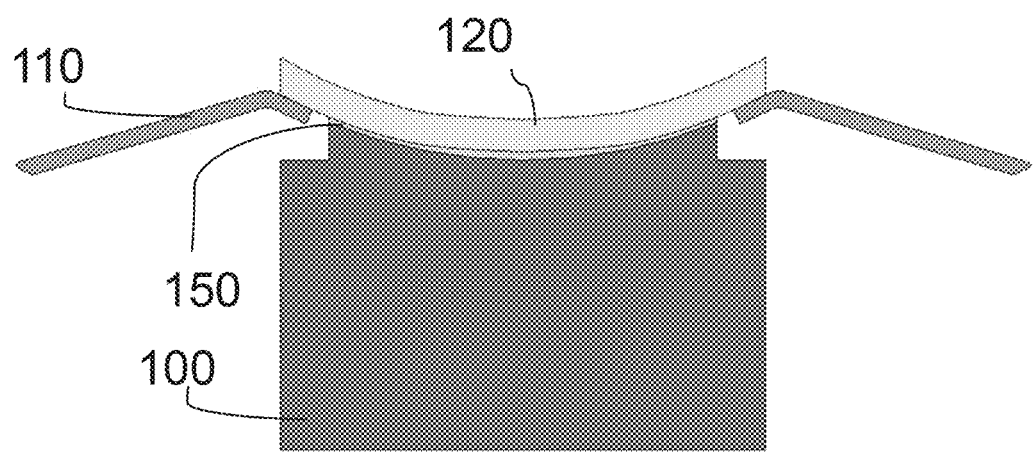
FIG. 5 shows the non-uniform bonding line between piezoelectric layer and backing layer in a conventional curved ultrasound transducer.

Referring to FIGS. 1, 2 and 3, a conventional probe is illustrated therein. The probe comprises an ultrasound waves emitting and receiving head 1, which has a front side from which the ultrasound waves are emitted in the direction against a target, such as a body under examination, and on which the reflected ultrasound waves or incoming ultrasound waves impinge and are sensed. The ultrasound head 1 has a back side 3 which is opposite to the said front side and which is oriented towards the inside of a probe casing and towards means for supporting the probe head provided inside the probe casing.

The probe head 1 comprises, in an order starting from the back side of the said head towards the front side of the said head, which order corresponds also to the direction of propagation of the emitted ultrasound waves, a first layer 101 formed by an array of contact electrodes. Each contact electrode of this layer 101 of contact electrodes has a separate electric connection line to a corresponding contact pin on a contact termination provided along at least one edge of the layer of contact electrodes and indicated with 201. The layer 101 of contact electrodes is typically in the form of an array of at least electrically separated contact electrodes since each one of the said contact electrodes has the function of feeding the electric excitation signal to the associated transducer and of collecting the electric receipt signal from the associated transducer when the said transducer is mechanically excited by an impinging ultrasound wave.

On the layer formed by the array of contact electrodes, an array of piezoelectric elements 301 is laid. Each one of the piezoelectric elements forms an emitting and receiving transducer. Piezoelectric elements are typically fabricated from lead zirconate titanate (PZT), PZT-resin composite or Single Crystal material. The single transducers are each one coincident and in electric contact with one of contact electrodes of the layer 101. In a possible configuration, a further layer of conductive material 401 is laid on the layer 301 formed by the array of transducers. The conductive material of the layer 401 is in electric contact with each one of the said piezoelectric elements and is connected to ground potential by means of a contact termination 501. The layer 401 of conductive material forms the ground electrode of the transducers of the layer 301. The layer 401 may be in the form of an array of ground electrodes, but since the ground potential is common to every of the transducers of the layer 301 there is no need to provide separate ground electrodes for each transducer, so that the said layer 401 can be easily formed by a continuous layer of conductive material. Alternatively, the ground connections may be formed by a microscopic section wire 401' contacting elements belonging to a same raw as shown in FIG. 3. Other ground connection geometries are obviously possible, such as, for example, of the so-called wrap-around type.

On the array of piezoelectric material elements 301 matching layers are provided which are indicated with numerals 601 and 701 in FIGS. 1 and 2. These layers (two in the example of FIG. 2, one in FIG. 3) have the function of adapting the acoustic impedance of the piezoelectric elements to the acoustic impedance of the target. Normally two or three layers are used in order to provide a progressive stepwise adaptation, which also allows to maintain a sufficiently large bandwidth for the passing ultrasound waves. In each material, the acoustic impedance is given by the product of density times speed of sound and can be considered equivalent to the electrical impedance for an electrical circuit with many power transfer stages. The thickness of each matching layer generally follows the $\lambda/4$ rule, so they depend on their operating frequency (generally from 2 MHz to 12 MHz for standard imaging probes) and speed of sound in each material. Matching layer are generally manufactured from epoxy resin loaded with metallic particles. In the configuration with grounded conductive layer 401 (see FIGS. 1 and 2) the first matching layer 601 is generally placed above such grounded layer 401. In case of wiring connection 401' as in FIG. 3, the first matching layer 601 is in direct contact with the piezoelectric elements 301.

Typically, the first matching layer 601 is made of a material having an acoustic impedance of about 5 to 12 MRayl and the last matching layer 701 has an acoustic impedance of about 2 MRayl.

As a last element, on the matching layer 701, an acoustic lens 801, typically of silicone rubber, is placed which forms the interface between the head of the probe 1 and the surface of a target body.

The contact terminations 201 and 501 of the layer 101 formed by the array of contact electrodes and of the layer 401 or wires 401' formed by the grounded conductive material are electrically and mechanically connected to a printed circuit board 4 which provides the necessary conductive tracks which are connected to a probe connection cable (not shown) via connector and which cable connects the probe with an ultrasound apparatus as for example an ultrasound imaging apparatus.

A multi-element ultrasonic transducer array is generally formed from a block of piezoelectric material, which may be either a ceramic or a polymer. The block is cut or diced into one or more rows of individual elements to form the array. The element-to-element spacing is known as the "pitch" of the array and the spaces between individual elements are known as "kerfs." The kerfs may be filled with some filler material, generally a damping material having low acoustic impedance that blocks and absorbs the transmission of vibrations between adjoining elements, or they may be air-filled. The array of elements may be left in a linear configuration in which all of the elements are in a single plane, or the array may be bent or curved for use as a convex or concave array.

Before the piezoelectric material is diced into individual array elements it is generally coated with metallic electrode material on the top (also referred to as the front or transmit/receive side) and bottom of the bar. The electrodes on the top of the elements are conventionally connected to an electrical reference potential or ground, and individual conductors are attached to electrode areas on the bottom of the bar to electrically connect to each subsequently formed element. These conductors are then conventionally potted in an acoustic backing material as described, for example, in U.S. Pat. No. 4,825,115 which fills the space below the transducer elements and between the wires, and damps acoustic vibrations emanating from the bottom of the transducer array. Alternately, the conductors and backing material may be preformed in a block of backing material containing parallel spaced wires, which is then attached to the piezoelectric as described in U.S. Pat. Nos. 5,329,498 and 5,267,221. The piezoelectric bar and electrodes are then diced while attached to the backing material. As the bar is diced into individual elements, the metal plating is simultaneously cut into individual electrically separate electrodes for each transducer element. The transducer is completed by bonding front matching layers and the acoustic lens.

The result is a stack of layers starting from the backing 2 to the acoustic lens 801 as shown, for example, in FIGS. 2 and 3.

The backing material 2 acts both as a support and as a damping device for the back-travelling acoustic wave, to minimize reverberations and ringing. Backing material is generally a special hard rubber compound with poor thermal conductivity. A metallic, typically aluminium, block 3 acts as a support for the backing material 2. Where the term "backing" occurs it is understood as meaning a solid mass, of suitable geometry, on which the piezoelectric elements are mounted; when this component is excited by a voltage pulse, the oscillation is dampened and the reduction in the amplitude between successive oscillations depends on the material with which the component is combined.

By controlling the delay of the waveform exciting the transducer elements, an electronic focusing can be achieved in the so-called azimuthal plane, i.e. in the plane crossing orthogonally the array elements.

Focusing on elevation direction, i.e. the direction of the transducer array orthogonal to the electronically scanned azimuthal plane, can be achieved either by shaping the acoustic lens in the elevation direction or by curving the transducer layer along the elevation direction as disclosed in U.S. Pat. No. 5,792,058. This is particularly significate for so-called 1D transducers, i.e. for array elements disposed along the azimuth direction.

Also when focusing is achieved with an acoustic lens, a curved transducer array may be used to increase or decrease the active width in the elevation direction. This approach allows to maintain the same architecture of the acoustic stack by changing only the lens keeping the whole housing of the probe.

Figure 8:
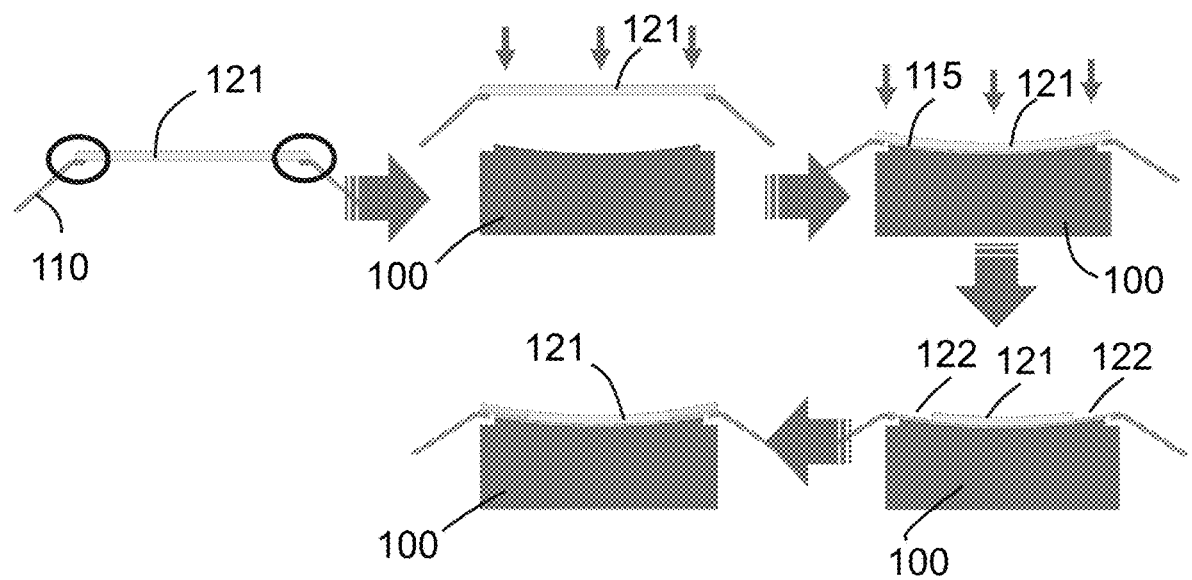
FIG. 8 graphically shows manufacturing process steps according to embodiments herein including a grinding operation of a piezoelectric material.
Figure 11:
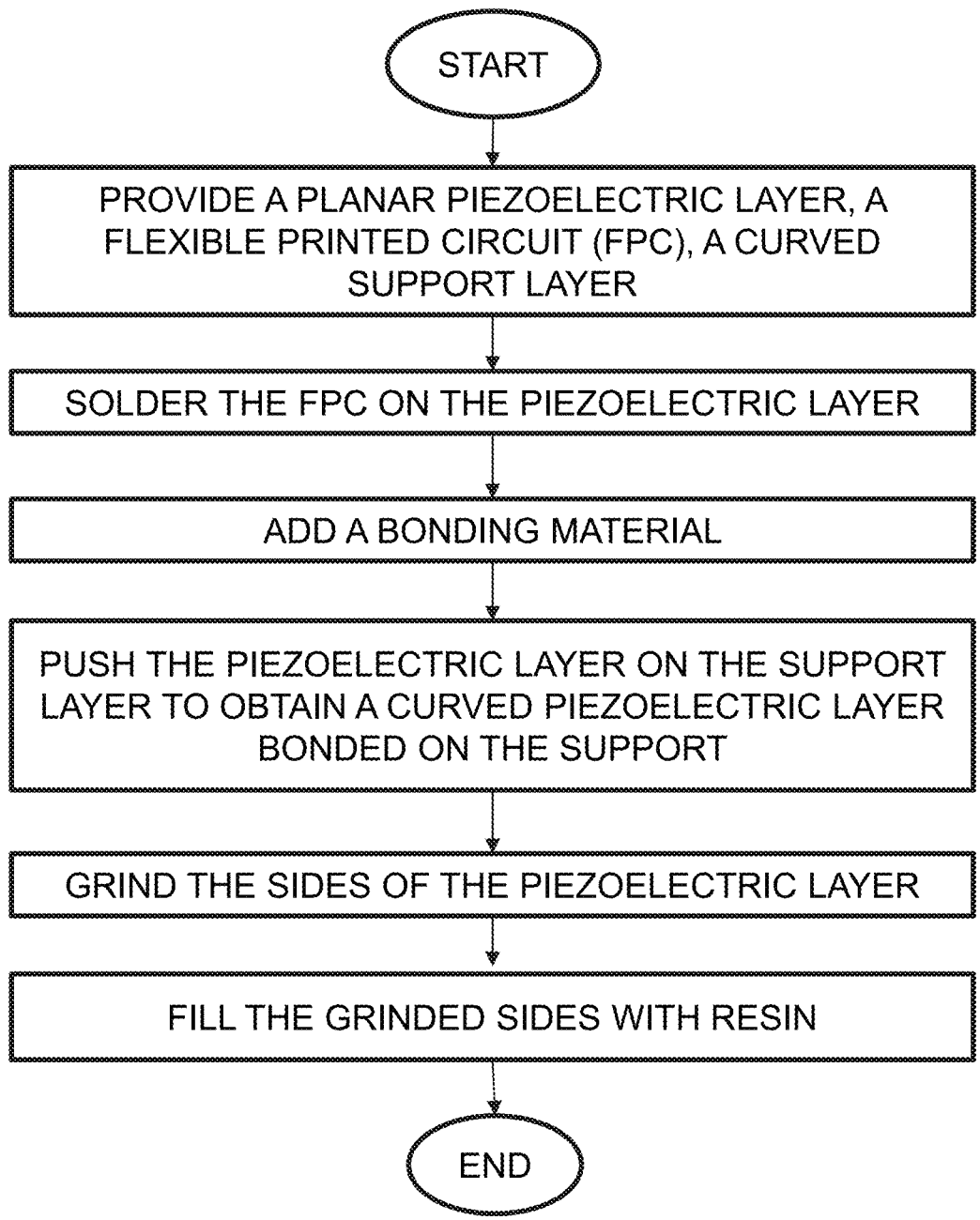
FIGS. 11, 12 and 13 are flowcharts of process for manufacturing a transducer assembly according to embodiments herein.

FIG. 8 and FIG. 11 show the sequence and the flowchart, respectively, of an exemplary process for manufacturing an acoustic stack according to a first embodiment.

The electrical connection 110, like for example a flexible printed circuit (FPC), is initially soldered on piezoelectric layer 121. Such piezoelectric layer is then stacked on the backing layer 100 with interposition of a bonding material 115. The bonding operation may be carried out using non-conductive adhesive. The force, schematically represented by arrows in FIG. 8, pushing the backing onto the piezoelectric layer or equally the piezoelectric layer onto the backing, determines the curvature of the piezoelectric layer 121 which is advantageously made of composite. The sides 122 of the piezoelectric layer 121 are then grinded or etched by means of mechanical dicing or laser dicing. The aim is to leave some microns of the piezoelectric layer also in the lateral part without removing completely the material. The so formed grooves are filled with resin (e.g. epoxy resin) which are optionally grinded in order to recover a smooth surface.

At the end of the above-mentioned manufacturing process the two smooth sides can be covered by metal ink (e.g. silver ink), in order to recover the electrical continuity on the overall surface. The result is the transducer assembly shown in FIG. 6.

Figure 13:
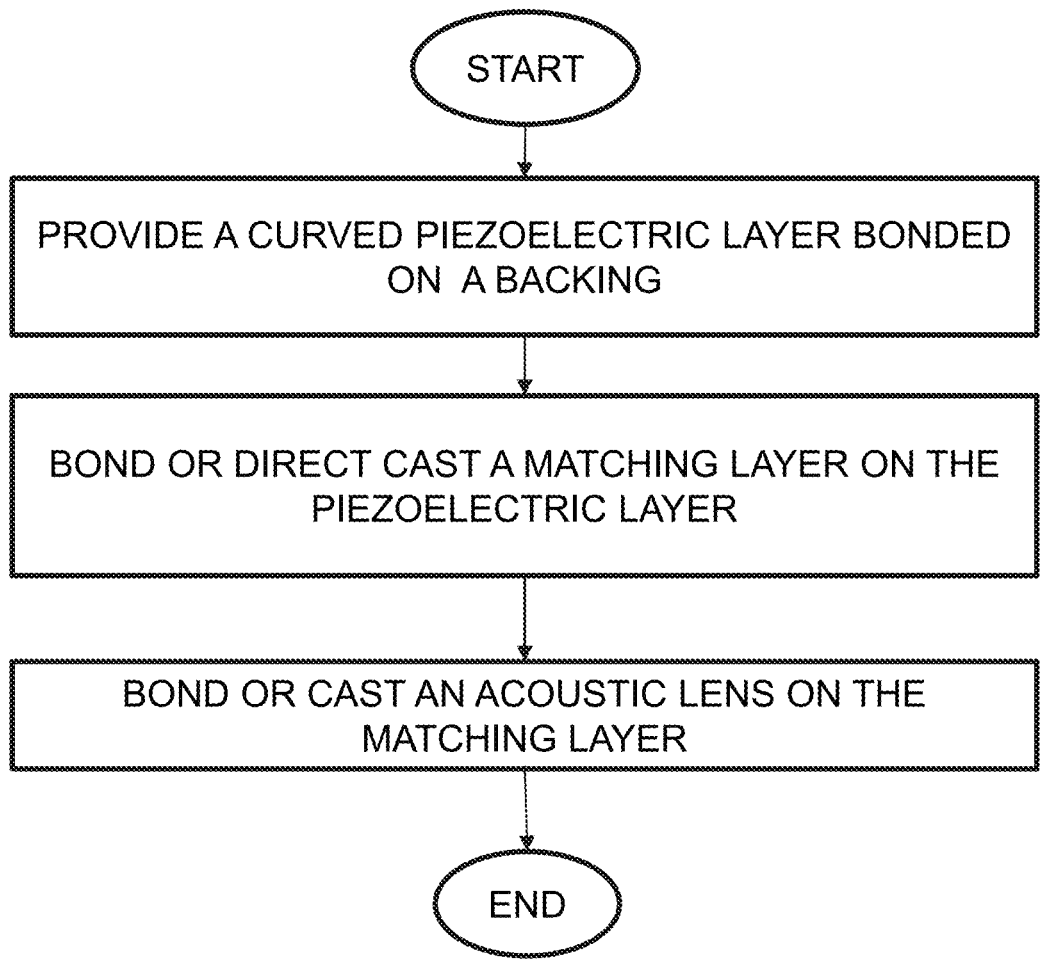

The overall workflow of the manufacturing process for the entire acoustic stack with the decreased elevation of the piezoelectric layer is shown in FIG. 13. Following the sequence, the next step is the bonding of the matching layer 130 on the piezoelectric layer 121 and then the bonding of pre-fabricated lens 140 with non-conductive adhesive on the matching layer 130.

Figure 7:
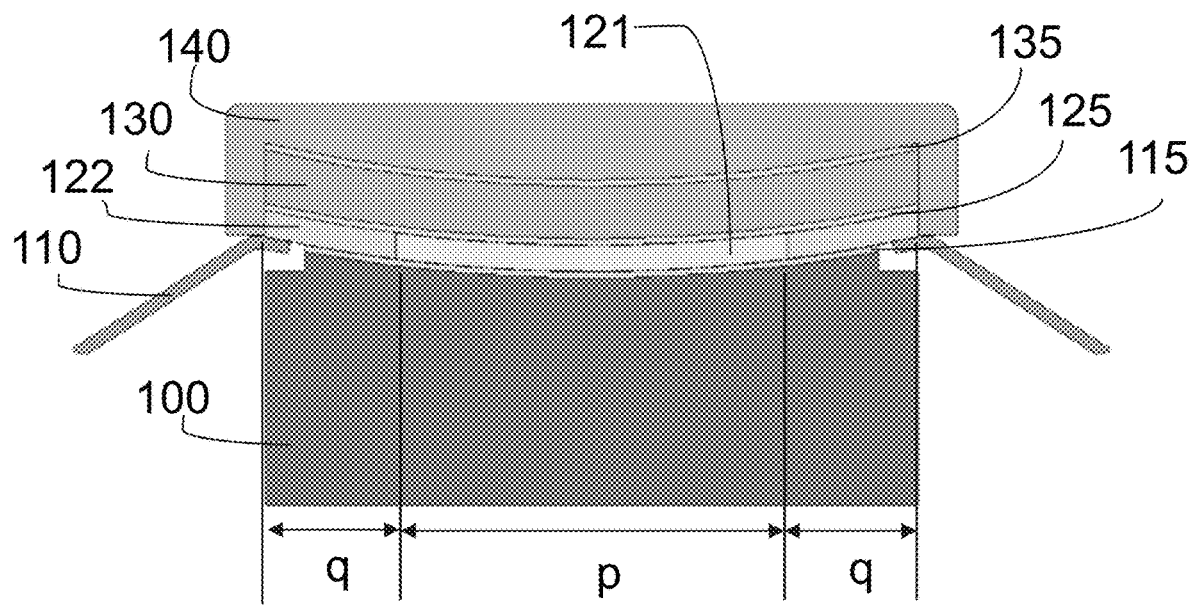
FIG. 7 shows an acoustic stack including the transducer assembly of FIG. 6.

The layers 115, 125 and 135 shown in FIG. 7 are the bonding lines.

It should be noted that the process of manufacturing of the acoustic stack according to this embodiment is not limited to the sequence described above and may be performed in any meaningful different sequence. The matching layer(s) 130 could also be poured directly on the piezoelectric layer. Lens 140 may be formed by means of mold (injection of material with low acoustic impedance like the human skin, e.g. silicone).

Any possible combination of bonding/casting of layers is to be considered included in the present disclosure to arrive at the stack shown in FIG. 7 including backing 100, piezo material 121, matching layer 130 and lens 140.

For example, layers may be bonded/casted in pairs and the resultant subassemblies bonded together.

The width "p" of the piezoelectric layer 121 is obtained ad-hoc for the requested elevation and is preferably in the range [1÷4] mm. The width "q" is the non-piezoelectric part of the piezoelectric layer and the values are in the range [0.5÷2] mm. Therefore, the overall width (q+p+q) of the composite is preferably in the range [1.5÷6] mm, but not limited to these dimensions.

Although well performing its duties, the repeatability of the manufacturing process described so far is relatively poor due to the grinding operations that are affected by high risk in terms of scraps and reproducibility.

Figure 9A:
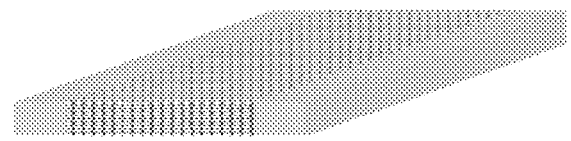
FIGS. 9A and 9B show the structure of a composite-based piezoelectric element for manufacturing a transducer assembly according to further embodiments.
Figure 9B:
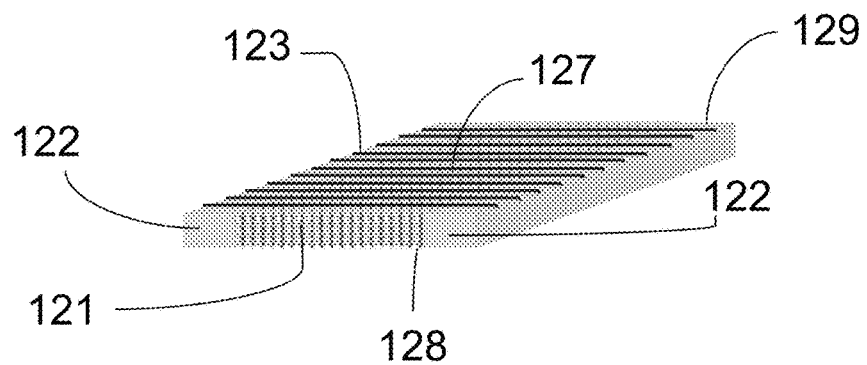

The high number of the steps can be reduced by using a piezoelectric layer composed by composite in the middle (matrix between piezoelectric material and resin) as shown in FIGS. 9A and 9B.

The composite 121 generates the piezoelectric effect with the required elevation, typically from 1 to 5 mm. The two sides 122 are composed by resin (e.g. epoxy resin, non-conductive resin). The piezoelectric layer is plated by metal layer (e.g. gold) 129 for guarantying the electrical connection. The gold electrode can be deposited by plating or by CVD (Chemical Vapour Deposition) on both surfaces (+ side 127, and − side 128) and/or wraparound configuration.

The kerf 123 allows for the electrical separation (electrical insulation) between the composite elements for the generation of the piezoelectric elements array. The separation is provided by the mechanical dicing or laser dicing, in which the metal plating (some nano-meters of thickness) is completely removed.

Figure 6:
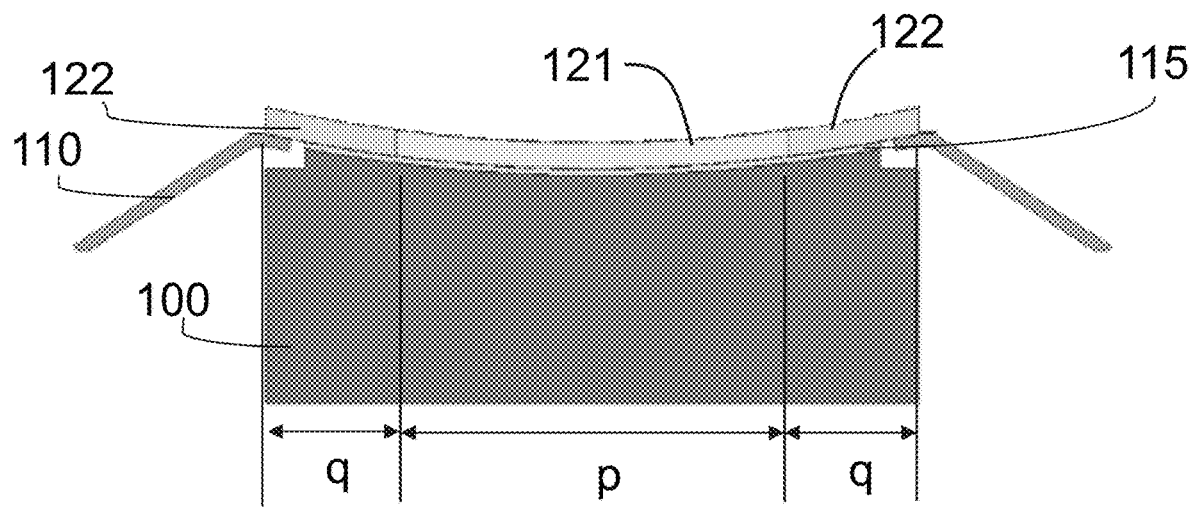
FIG. 6 schematically shows the cross section of a transducer assembly according to embodiments herein.

The structure of the piezoelectric assembly is the same as shown in FIG. 6, but the improvement consists in a stand-alone component, that allows for higher yield and process repeatability within the lower number of process steps.

By choosing such component is thus possible to achieve different elevation focussing without changing the shape and dimensions of the probe particularly the width of the backing, the matching layer(s) and the acoustic lens, as well as of any other layer that may be included in the final stack such as a de-matching layer to be placed between the backing and the piezo to improve overall thermal management and/or sensitivity.

Figure 10:
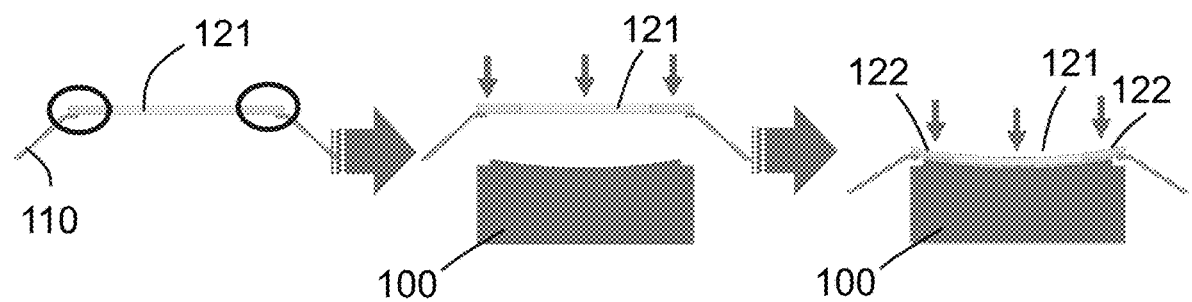
FIG. 10 graphically shows process steps according to embodiment herein for manufacturing a transducer assembly including the composite-based piezoelectric element of FIGS. 9A and 9B.
Figure 12:
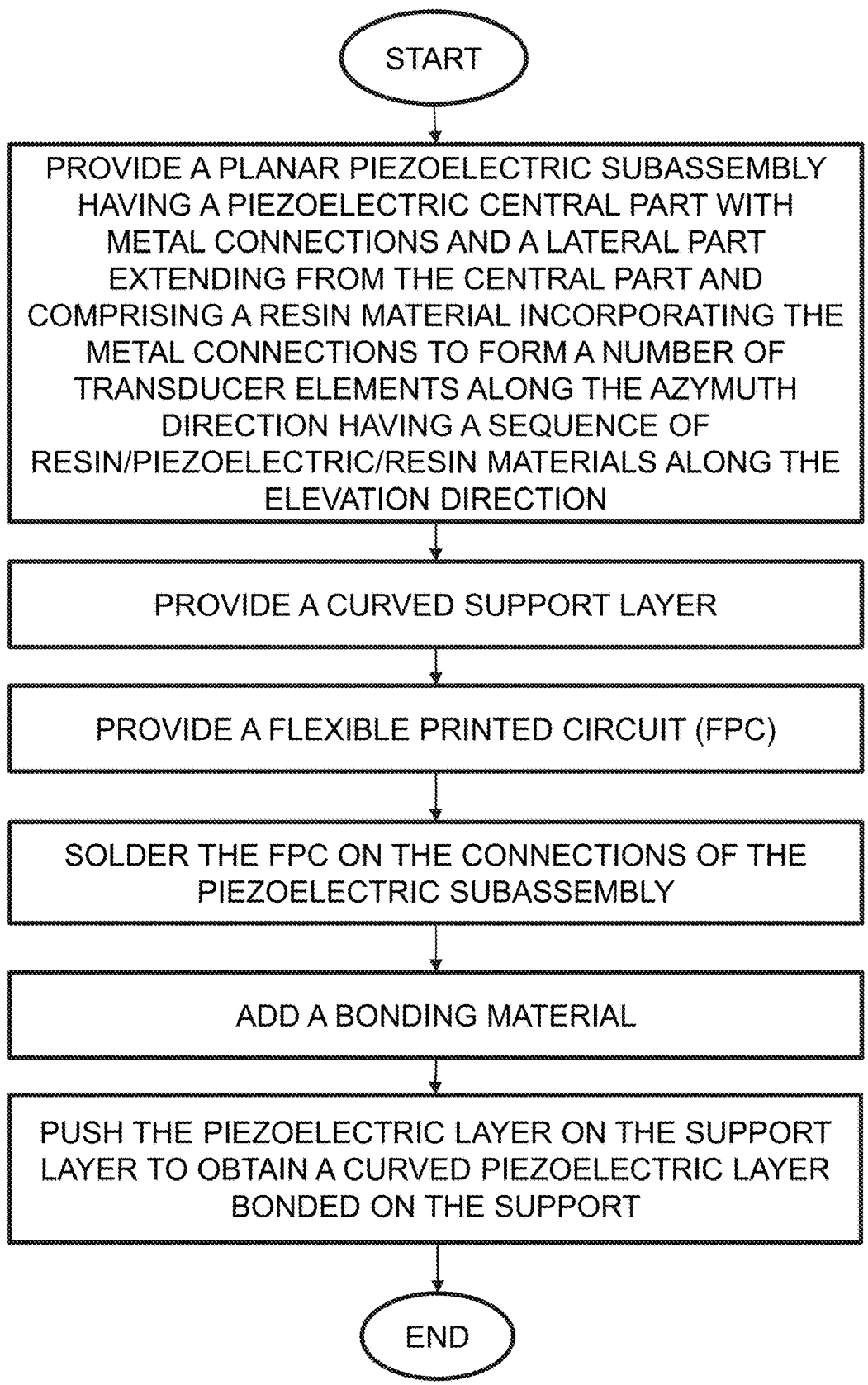

FIG. 10 and FIG. 12 show the sequence and the flowchart, respectively, of an exemplary process for manufacturing an acoustic stack according to a second embodiment. In this case grinding/etching steps are omitted as the piezoelectric subassembly has already the required form and shape.

It is thus enough to push the piezoelectric layer 121 having a lateral part in resin 122 onto a curved backing 100 with interposition of a bonding material 115 to obtain the desired tunable transducer subassembly with a quick, simple and accurate high yield manufacturing process.

Several options are possible for forming the acoustic stack based on the stand-alone composite layer.

In an embodiment, the process comprises:
bonding or casting the matching layer on the piezoelectric layer;
bonding or casting the lens layer on the matching layer.

In another embodiment, the process comprises:
bonding the piezoelectric layer and the matching layer in a single operation;
bonding the matching layer and the lens layer in a single operation.

In any case, the result is a piezoelectric subassembly with tunable elevation, i.e. with the possibility to change the elevation of the piezoelectric layer without changing the architecture of the acoustic stack.

Figure 14:
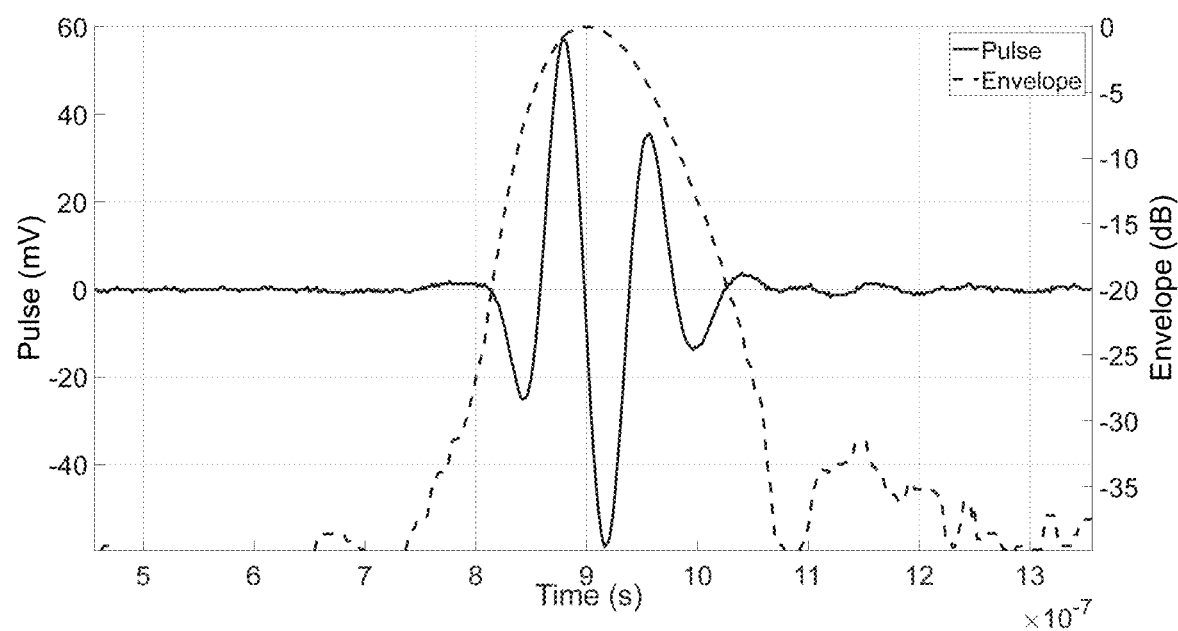
FIG. 14 shows of the pulse (mV) and its envelope (dB) provided by a transducer having central operating frequency below 15 MHz and above 8 MHz, starting from the composite-based piezoelectric element of FIGS. 9A and 9B and manufactured by process steps as described in FIG. 10, FIG. 12 and FIG. 13.

By the way of example only, FIG. 14 shows that the transducer having a central operating frequency below 16 MHz and above 8 MHz, manufactured by the process according to the embodiment as disclosed with reference to FIGS. 10, 12 and 13, provides proper impulse response. In this example, the piezoelectric layer has thickness in the range 70÷180 μm and acoustic impedance in the range 12÷16 Mrayl and the resin viscosity ranges between 500 cps and 8000 cps.

The invention claimed is:

1. Kit comprising a curved backing layer having a predetermined curvature and a plurality of piezoelectric subassemblies in respective ones of transducer assemblies, the plurality of piezoelectric subassemblies having the same dimensions but different central part/lateral part area ratio as each other to implement different elevation focusing within transducer assemblies of the same dimensions, the plurality of peizoelectric subassemblies each being configured according to a piezoelectric subassembly comprised in a corresponding one of the transducer assemblies that is operable to transmit ultrasonic energy in a desired direction towards a zone adapted to be acoustically coupled to an object or area of interest,
wherein the piezoelectric subassembly matches a curved support layer disposed behind the piezoelectric subassembly with respect to the desired direction,
wherein the piezoelectric subassembly comprises piezoelectric elements and metal connections, wherein the piezoelectric elements are disposed along a first direction, so-called azimuth direction (A), to form a number of parallel curved segments of piezoelectric elements extending in a second direction, so-called elevation direction (E), each piezoelectric segment being in contact with a corresponding metal connection extending in the elevation direction for transmitting/receiving electric signals to/from each piezoelectric segment,
wherein the piezoelectric subassembly comprises a central part and a lateral part extending from the central part, wherein the central part comprises piezoelectric material and the lateral part comprises a resin material incorporating the metal connections so that each curved segment results substantially in a sequence of resin/piezoelectric/resin materials disposed along the elevation direction (E) with the extension and curvature of the piezoelectric material disposed in the central part of the subassembly defining the elevation focussing of the transducer assembly, wherein the relation between area covered by the central part and area covered by the lateral part is a function of an aperture of the transducer assembly in the elevation direction.

2. Kit comprising a curved backing layer having a predetermined curvature and a plurality of peizoelectric subassemblies in respective ones of transducer assemblies, the plurality of piezoelectric subassemblies having the same dimensions but different central part/lateral part area ratio as each other to implement different elevation focussing within the respective transducer assemblies of the same dimensions, the plurality of piezoelectric subassemblies each being configured according to a piezoelectric subassembly comprised in a corresponding one of the transducer assemblies that is operable to transmit ultrasonic energy in a desired direction towards a zone adapted to be acoustically coupled to an object or area of interest,
wherein the piezoelectric subassembly matches a curved support layer disposed behind the piezoelectric subassembly with respect to the desired direction,
wherein the piezoelectric subassembly comprises piezoelectric elements and metal connections, wherein the piezoelectric elements are disposed along a first direction, so-called azimuth direction (A), to form a number of parallel curved segments of piezoelectric elements extending in a second direction, so-called elevation direction (E), each piezoelectric segment being in contact with a corresponding metal connection extending in the elevation direction for transmitting/receiving electric signals to/from each piezoelectric segment,
wherein the piezoelectric subassembly comprises a central part and a lateral part extending from the central part, wherein the central part comprises piezoelectric material and the lateral part comprises a resin material incorporating the metal connections so that each curved segment results substantially in a sequence of resin/piezoelectric/resin materials disposed along the elevation direction (E) with the extension and curvature of the piezoelectric material disposed in the central part of the subassembly defining the elevation focussing of the corresponding transducer assembly.

3. Transducer assembly according to claim 2, wherein the central part of the subassembly comprises more than 90% of the whole piezoelectric material forming the subassembly.

4. Transducer assembly according to claim 3, wherein the central part of the subassembly comprises more than 95% of the whole piezoelectric material forming the subassembly.

5. Transducer assembly according to claim 3, wherein the central part of the subassembly comprises more than 97% of the whole piezoelectric material forming the subassembly.

6. Transducer assembly according to claim 2, wherein the central part of each curved segment of the subassembly occupies an area having an extension which varies from 40% to 70% of the whole extension of the curved segment.

7. Transducer assembly according to claim 6, wherein the central part of the curved segment of the subassembly occupies an area having an extension which varies from 50% to 60% of the whole extension of the curved segment.

8. Transducer assembly according to claim 2, wherein the transducer subassembly is a matrix of composite material and resin material with the composite material substantially located in the middle of the subassembly to form the active part of the transducer assembly for transmitting/receiving electric signals, the matrix having a side facing the support layer with interposition of a bonding material.

9. Ultrasound probe comprising an acoustic lens and a matching layer stacked over a transducer assembly according to claim 2, the transducer assembly having a ratio between the central and the lateral part function of the acoustic/geometric characteristics of the acoustic lens.

10. Composite-based piezoelectric subassembly for manufacturing a transducer assembly according to claim 2, the subassembly comprising a planar composite-based element having a piezoelectric central part with metal connections and a lateral part extending from the central part and comprising a resin material incorporating the metal connections to form a number of transducer elements along a first direction, so-called azimuth direction (A), having a sequence of resin/piezoelectric/resin materials along a second direction, so-called elevation direction (E), wherein the relation between area covered by the central part and area covered by the lateral part is a function of the aperture of the transducer assembly to be manufactured.

* * * * *